United States Patent [19]

Kampf et al.

[11] Patent Number: 4,512,926
[45] Date of Patent: Apr. 23, 1985

[54] PROCESS FOR THE SILYLATION OF UNSATURATED, NATURALLY OCCURRING OILS OR THE INTERESTERIFICATION PRODUCTS THEREOF

[75] Inventors: Wolfgang Kampf, Haltern; Roland Streck; Horst G. Haag, both of Marl, all of Fed. Rep. of Germany

[73] Assignee: Chemische Werke Huels AG, Marl, Fed. Rep. of Germany

[21] Appl. No.: 396,217

[22] Filed: Jul. 8, 1982

[30] Foreign Application Priority Data

Aug. 7, 1981 [DE] Fed. Rep. of Germany ....... 3126845

[51] Int. Cl.$^3$ ..................... C07C 53/22; C07C 57/00; C07C 57/12
[52] U.S. Cl. .................... 260/398; 260/405; 260/407; 260/408; 260/409; 260/410; 260/410.7; 260/410.9 R; 260/413; 556/419; 556/466
[58] Field of Search ............... 260/407, 408, 409, 410, 260/410.7, 410.9 R, 405, 413, 398; 556/466, 419

[56] References Cited

U.S. PATENT DOCUMENTS 3,857,825 12/1974 Streck et al. .................... 260/88.1 R
4,176,127 11/1979 Hempel et al. ....................... 260/407
4,183,844 1/1980 Streck et al. ...................... 260/42.15

*Primary Examiner*—Paul F. Shaver
*Attorney, Agent, or Firm*—Millen & White

[57] ABSTRACT

A process for the silylation of unsaturated, naturally occurring oils or the interesterification products thereof, comprises reacting the unsaturated, naturally occurring oils or the interesterification products thereof, at a temperature of 200°–350°C. under inert gas, with silicon compounds of Formula I

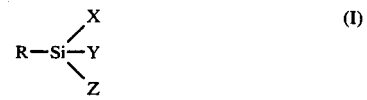

wherein
R is hydrogen or an unsaturated aliphatic hydrocarbon residue of 2–6 carbon atoms,
X is a hydrolyzable residue, and
Y and Z independently are one of the X groups, alkyl of 1–8 carbon atoms, cycloalkyl of 5–12 carbon atoms, or optionally substituted phenyl.

6 Claims, No Drawings

PROCESS FOR THE SILYLATION OF UNSATURATED, NATURALLY OCCURRING OILS OR THE INTERESTERIFICATION PRODUCTS THEREOF

BACKGROUND OF THE INVENTION

It is known to introduce reactive silyl groups into unsaturated, naturally occurring oils for certain uses, for example, when they are used as curing agents for bonding agents based on alkali metal silicates.

As disclosed in DOS No. 2,752,973, for this purpose it is possible to react hydrogen silanes with oleic acid esters or corresponding esters of linoleic acid in the presence of a catalyst at temperatures of above 50° C. Suitable catalysts are, in particular, platinum or chloroplatinic acid, azo compounds, organo-metallic compounds, as well as peroxides. To improve the conversion rates, DOS No. 2,752,973 proposes first to partially hydrogenate the oleic acid esters employed and thereafter to react the partially hdyrogenated reaction product with hydrogen silanes in the presence of organic peroxides.

The disadvantages of the prior art processes include the need for relatively expensive catalysts and in certain cases additional process stages, e.g., to remove the catalysts to lessen unavoidable contamination of the products therewith.

SUMMARY OF THE INVENTION

It is, therefore, an object of the present invention to provide a simple and economical process for preparing unsaturated, naturally occurring oils carrying reactive silyl groups, or the interesterification products thereof carrying reactive silyl groups.

Upon further study of the specification and appended claims, further objects and advantages of this invention will become apparent to those skilled in the art.

These objects have been achieved by this invention by providing a process for the silylation of unsaturated, naturally occurring oils or the interesterification products thereof, comprising reacting, at a temperature of 200°-350° C. and under an inert gas, the unsaturated, naturally occurring oils or the interesterification products thereof with silicon compound of Formula I

wherein

R is hydrogen or an unsaturated aliphatic hydrocarbon residue of 2-6 carbon atoms, X is a hydrolyzable residue, and Y and Z independently are one of the X groups, alkyl of 1-8 carbon atoms, cycloalkyl of 5-12 carbon atoms, or optionally substituted phenyl.

DETAILED DISCUSSION

Primarily useful in the process of this invention as the unsaturated, naturally occurring oils or their interesterification products are those based primarily on esters derived from oleic acid, linoleic acid and linolenic acid. Others, of course, are suitable. Such esters are present in many vegetable and animal oils, such as for example, olive oil, peanut oil, sesame oil, corn oil, sunflower oil, poppy-seed oil, cottonseed oil, soybean oil, linseed oil, rapeseed oil, fish oil, and whale oil. Insofar as it is desired not to use the oils in the form of their triglyceride esters, before the reaction of this invention with the silicon compound, it is possible to conduct an ester interchange with other alcohols, preferably monohydric ones such as, for example, methanol (See, e.g., Ullmanns Encyclopaedie der technischen Chemie (Ullman's Encyclopedia of Technical Chemistry) 7: 526 (1956)) whose disclosure is incorporated by reference herein.

Specific structural and compositional details of these naturally occurring oils are not critical.

According to this invention, the reactive silyl groups are introduced into the unsaturated, naturally occurring oil by reaction with a silicon compound of Formula I. In Formula I, r is an unsaturated aliphatic hydrocarbon residue of 2-6, preferably 2-4 carbon atoms; X is a hydrolyzable residue, such as, for example, halogen, preferably chlorine or bromine, alkoxy or alkoxyalkoxy, preferably of up to 4 carbon atoms, aryloxy, preferably of 6-12 carbon atoms, carboxylate, based on a hydrocarbon, e.g., alkanoyloxy, preferably of up to 8 carbon atoms, ketoximato based on a hydrocarbon, preferably of up to 6 carbon atoms in the keto group, or based on a hydrocarbon preferably of up to 12 carbon atoms. Equivalents of these X groups are also included. Y and Z can be the same as X, i.e., chosen from the X groups independently of each other, but in addition can also be alkyl of 1-8 carbon atoms, cycloalkyl of 5-12 carbon atoms, or an optionally substituted pehnyl e.g., phenyl or phenyl substituted by halogen and/or alkyl.

Typical representatives of the unsaturated organosilanes include, for example, vinyltrichlorosilane, vinyltrimethoxysilane, vinyltriethoxysilane, vinyltris-(methoxyethoxy)silane, vinylmethyldimethoxysilane, vinyldimethylchlorosilane, allylmethylbutylchlorosilane, allylethyldibromosilane, allyldimethylacetoxysilane, allyltriisopropoxysilane, allylphenyldiphenoxysilane, methallylbutylchlorobromosilane, crotylmethylpropyliodosilane, and vinyldimethylketoximatomethoxychlorosilane.

Preferred are vinyl- and allylsilanes with halogen atoms or alkoxy groups as the hydrolyzable residues X, for example, vinyltrichlorosilane, vinyldichlorosilane, vinylmethylethylchlorosilane, vinyltrimethoxysilane, vinyltriethoxysilane, vinylmethyldimethoxysilane, allyltribromosilane, and allylethylmethoxypropoxysilane.

Among the unsaturated halosilanes, those with chlorine as the halogen are, in turn, preferred, so that especially preferred are, for example, vinyltrichlorosilane, vinylmethyldichlorosilane, vinyldimethylchlorosilane, and allyltrichlorosilane.

The chlorosilyl groups introduced by these compounds can possibly be converted into other reactive silyl groups, for example, during the course of the working-up process, e.g., by the addition of, preferably, alcohols, trialkyl orthoformates, epoxides, sodium acetate, etc., according to known prior art reactions.

From the class of compounds of unsaturated alkoxysilanes, those having alkoxy residues of 1-4 carbon atoms are especially advantageous, so that especially preferred are vinyltrimethoxysilane, vinyltriethoxysilane, vinylmethoxydiethoxysilane, vinylmethylmethoxypropoxysilane, allylpropylpropoxybutoxysilane etc. Quite especially preferred is the use of vinyltrimethoxysilane.

With the use of these unsaturated alkoxysilanes, the advantage is achieved that working up of the chemical addition products can practically be entirely eliminated or can be restricted, in any event, to the removal of any existing residues of unreacted alkenylalkoxysilane by distillation. No catalyst residues need be of concern.

The chemical addition reaction between the unsaturated, naturally occurring oils and/or the interesterification products thereof and the unsaturated silicon compounds of Formula I is conducted by heating the reactants to temperatures of 200°–350° C., preferably 250°–330° C. under an inert gas. The unsaturated silane is suitably used in a molar excess. Molar ratios of silane to oil of 1–15:1, preferably 2–10:1, are customary. Typical reaction times are 2–20 hours, preferably 5–15 hours, depending on the reaction temperature selected. No catalyst is required.

Increased pressure is required for the chemical addition only insofar as the vapor pressure of the unsaturated silane at the selected reaction temperature is >1 bar. The chemical addition of the unsaturated silane to the unsaturated, naturally occurring oil and/or its interesterification product can also be carried out in the presence of an organic solvent. In this case, care must be taken that the apparatus is designed for the pressure which may build up.

The reaction can also be conducted in the presence of conventional stabilizers in amounts effective to prevent spontaneous reactions of the silane.

Normally, the addition products obtained according to the process of this invention are simply worked up by vacuum evaporation of any unreacted silane and any solvent which are present.

The chemically added amount of unsaturated silane and thus the number of reactive silyl groups present on the average in the addition product can be adjusted by routine selection of the quantity of silane feed. The selected amount is primarily dependent on the specific end use of the addition product. In general, addition products are prepared according to the process of this invention with 3–15% by weight, preferably 6–12% by weight, of silicon.

The addition products produced in accordance with the process of this invention can be conventionally utilized, for example, as additives to improve the properties of adhesives, cements, sealing and caulking compounds, as agents for dispersion of pigments, for rendering substrates hydrophobic, such as paper, textile materials, wood, cardboard, and building materials, as well as for soil stabilization. Their contents as additives in such compositions are usually 0.1–10%, preferably 1–5% by weight based on the total weight of the resultant compositions.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

As a test for the incorporation of the analytically determined silicon into the natural oil, the crosslinkability by water is determined. For this purpose, 2.0 g of the product is dissolved in 40 ml of hexane, 1.0 ml of a 5% solution of dibutyltin dilaurate in hexane is added, and the solution is poured on water in a dish (surface area 600 cm$^2$). After standing for 24 hours at room temperature, a solid polymer film has formed; the proportions of this film insoluble in toluene at room temperature (25° C.) are measured after a preceding drying step.

EXAMPLE 1

100 g of linseed oil (viscosity of 46.7 mPa·s, iodine number 180) was maintained in an autoclave under a nitrogen atmosphere together with 200 g of vinyltrimethoxysilane (VTMOS) for 15 hours at 260° C. The mixture was agitated during this period. The amount of silane, with complete chemical addition to the oil, corresponded to a Si content of the product of 12.65% Si. An oil was obtained having 9.6% Si after a subsequent one-hour vacuum treatment at 130° C. Accordingly, 76% of the silane employed was contained in the product.

The iodine number, measured according to DIN 53 241, page 1, was 96; the viscosity was 208 mPa·s (20° C.), and the gel content was <2%. Per the crosslinking test, the product had 92% insoluble proportions.

EXAMPLES 2–5

125 g of linseed oil having the characteristic data set forth in Example 1 was maintained in an autoclave for various periods of time at 270° C. under a nitrogen atmosphere, together with 175 g of vinyltrimethoxysilane. The results are shown in Table 1.

TABLE 1

| Example | Time [h] | Si [%] | Conversion [%] | Gel [%] | Viscosity [mPa·s] |
|---|---|---|---|---|---|
| 2 | 3 | 6.0 | 52.8 | 50 | 140 |
| 3 | 5 | 7.0 | 63.1 | 77 | 151 |
| 4 | 10 | 8.8 | 79.8 | 85 | 307 |
| 5 | 15 | 10.7 | 84.7 | 91 | 338 |

The values in the "Conversion" column refer to silicon found versus silicon used.

EXAMPLES 6–16

The reaction of vinyltrimethoxysilane with linseed oil was conducted at varying temperatures. The results are listed in Table 2.

TABLE 2

| Example | T [°C.] | t [h] | VTMOS [g] | Linseed Oil [g] | Si [%] | Conversion [%] | Gel [%] | Viscosity [mPa·s] |
|---|---|---|---|---|---|---|---|---|
| 6 | 250 | 15 | 100 | 200 | 2.9 | 45.5 | 73 | 301 |
| 7 | 260 | 15 | 125 | 175 | 5.1 | 64.4 | 67 | 2530 |
| 8 | 260 | 15 | 150 | 150 | 6.4 | 67.6 | 76 | 763 |
| 9 | 260 | 15 | 175 | 125 | 8.2 | 74.2 | 89 | 316 |
| 10 | 260 | 15 | 200 | 100 | 9.6 | 76.0 | 92 | 208 |
| 11 | 270 | 15 | 150 | 150 | 8.1 | 84.9 | 81 | 930 |
| 12 | 280 | 5 | 200 | 100 | 10.6 | 84.0 | 83 | 158 |
| 13 | 290 | 5 | 200 | 100 | 10.2 | 80.7 | 87 | 205 |
| 14 | 300 | 5 | 200 | 100 | 10.9 | 86.2 | 88 | 333 |
| 15 | 310 | 5 | 200 | 100 | 10.6 | 83.8 | 85 | 267 |

TABLE 2-continued

| Example | T [°C.] | t [h] | VTMOS [g] | Linseed Oil [g] | Si [%] | Conversion [%] | Gel [%] | Viscosity [mPa·s] |
|---|---|---|---|---|---|---|---|---|
| 16 | 320 | 5 | 200 | 100 | 11.1 | 87.7 | 87 | 418 |

The test results were no different in experiments wherein the stabilizer tert-butyl pyrocatechol (1000 ppm) was added to prevent spontaneous reaction of the Si compound.

EXAMPLES 17–25

Instead of linseed oil, other oils were reacted with vinytrimethoxysilane. These were a vegetable oil (iodine number 115; viscosity 70.5 mPa·s at 20° C.; 3.83 cis-positioned double bonds per molecule); a sunflower oil (iodine number 135; viscosity 60.2 mPa·s at 20° C.; 4.73 cis-positioned double bonds per molecule); and a soybean oil (iodine number 133; viscosity 59.7 mPa·s at 20° C.). The results are set forth in Table 3.

EXAMPLES 26–29

The unsaturated materials employed were oleic acid methyl ester (viscosity 6.26 mPa·s at 20° C.), as well as oleic acid triglyceride (viscosity 83.1 mPa·s at 20° C.). The results are compiled in Table 4.

EXAMPLE 30

In place of VTMOS, SiHCl₃ was employed; the SiH-grouping was to be chemically added to the double bond. Under agitation, 150 g of the vegetable oil of Examples 17–19 was maintained with 150 g of SiHCl₃ at 225° C. for 5 hours under an inert gas atmosphere. An oil resulted, after having been worked up analogously to Example 1, with 7.2% Si (68.1% conversion). The viscosity was 180 mPa·s (20° C.). The gel content per the crosslinking test was 78%.

EXAMPLE 31

Vinyltrichlorosilane was used as the Si compound to be added. Under test conditions analogous to Example 30 (225° C.; 5 hours), 150 g of vegetable oil and 150 g of Si compound were employed once more.

After evaporation of excess vinyltrichlorosilane under vacuum, an oil was obtained with 6.1% Si (70.3% conversion) and with a viscosity of 212 mPa·s (20° C.). The gel value per the crosslinking test was 89%.

The preceding examples can be repeated with similar success by substituting the generically or specifically described reactants and/or operating conditions of this invention for those used in the preceding examples.

From the foregoing description, one skilled in the art can easily ascertain the essential characteristic of this invention, and without departing from the spirit and scope thereof, can make various changes and modifications of the invention to adapt it to various usages and conditions.

We claim:

1. A process for silylating an unsaturated, naturally occurring oil or an interesterification product thereof, consisting essentially of reacting, at a temperature of 200°–350° C. and under an inert gas, the unsaturated, naturally occurring oil or an interesterification product thereof with a silicon compound of the formula

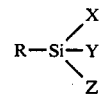

wherein
R is an unsaturated aliphatic hydrocarbon of 2–6 carbon atoms,
X is halogen, $C_{1-6}$-alkoxy, $C_{1-6}$-alkoxyalkoxy, $C_{6-12}$-aryloxy, $C_{1-8}$-alkanoyloxy, $C_{1-6}$-ketoximato or $C_{1-8}$-hydrocarbylamido,
Y and Z independently are one of the X groups, alkyl of 1–8 carbon atoms, cycloalkyl of 5–12 carbon atoms, or optionally substituted phenyl.

2. A process of claim 1, wherein, in the silicon compound, Y and Z are the same as X, and X is chlorine or alkoxy of up to 4 carbon atoms.

TABLE 3

| Example | Type of Oil | T [°C.] | t [h] | Weight Ratio Oil:Si | Si [%] | Conversion [%] | Gel [%] | Viscosity [mPa·s] |
|---|---|---|---|---|---|---|---|---|
| 17 | Vegetable Oil | 250 | 15 | 1:2 | 6.9 | 53.0 | 65 | 104 |
| 18 | " | 280 | 3 | 5:7 | 7.6 | 54.3 | 78 | 142 |
| 19 | " | 290 | 3 | 1:2 | 9.2 | 72.8 | 63 | 171 |
| 20 | Sunflower Oil | 250 | 12 | 1:2 | 6.5 | 51.4 | 54 | 114 |
| 21 | Sunflower Oil | 260 | 10 | 1:2 | 7.7 | 61.0 | 72 | 99 |
| 22 | Soybean Oil | 250 | 3 | 1:2 | 2.8 | 22.2 | 31 | 64.4 |
| 23 | Soybean Oil | 270 | 3 | 1:2 | 5.2 | 41.1 | 48 | 72.3 |
| 24 | Soybean Oil | 270 | 5 | 1:2 | 7.7 | 61.0 | 68 | 78.8 |
| 25 | Soybean Oil | 290 | 5 | 1:2 | 10.1 | 79.8 | 83 | 113 |

TABLE 4

| Example | Unsaturated Compound | T [°C.] | t [h] | Weight Ratio Unsat. Compd.:Si | Si [%] | Conversion [%] | Gel [%] | Viscosity [mPa·s] |
|---|---|---|---|---|---|---|---|---|
| 26 | O | 270 | 5 | 1:2 | 4.9 | 38.8 | 68 | 11.2 |
| 27 | O | 300 | 5 | 1:2 | 11.0 | 87.0 | 75 | 14.9 |
| 28 | Otr | 250 | 8 | 1:2 | 6.6 | 52.2 | 50 | 96.6 |
| 29 | Otr | 260 | 5 | 1:2 | 6.6 | 52.2 | 52 | 385 |

O = Oleic Acid Methyl Ester
Otr = Oleic Acid Triglyceride

3. A process of claim 1 or 2, wherein the silylation is conducted at a temperature of 250°–330° C.

4. A process of claim 1, wherein the oil comprises an ester of oleic, linoleic or linolenic acid.

5. A process of claim 4, wherein the ester is a methyl or triglyceride ester.

6. A process of claim 1, wherein the bound silicon content in the silylated oil is 3–15% by weight.

* * * * *